United States Patent
Evans et al.

(10) Patent No.: US 10,064,997 B2
(45) Date of Patent: Sep. 4, 2018

(54) ROTATABLE FINGER FLANGE FOR A SYRINGE

(71) Applicant: West Pharmaceutical Services, Inc., Exton, PA (US)

(72) Inventors: Christopher Evans, Long Valley, NJ (US); Brian Costello, Whitehouse Station, NJ (US); Christopher Gieda, Long Valley, NJ (US); Raymond Protasiewicz, Whippany, NJ (US)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 898 days.

(21) Appl. No.: 14/510,791

(22) Filed: Oct. 9, 2014

(65) Prior Publication Data

US 2016/0101238 A1    Apr. 14, 2016

(51) Int. Cl.
*A61M 5/315*    (2006.01)
*A61M 5/31*    (2006.01)

(52) U.S. Cl.
CPC ... *A61M 5/3137* (2013.01); *A61M 2005/3139* (2013.01)

(58) Field of Classification Search
CPC .................. A61M 5/31; A61M 5/3137; A61M 2005/3139
USPC .................................................. 604/187, 227
See application file for complete search history.

(56) References Cited

U.S. PATENT DOCUMENTS 5,925,032 A  *  7/1999  Clements ................ A61M 5/34
                                                        604/192
2012/0095438 A1    4/2012  Lanin et al.

FOREIGN PATENT DOCUMENTS

| JP | H09-173451 A | 7/1997 |
| WO | 2011021621 A1 | 2/2011 |
| WO | 2012154185 A1 | 11/2012 |

* cited by examiner

*Primary Examiner* — Edelmira Bosques
*Assistant Examiner* — Tiffany Legette-Thompson
(74) *Attorney, Agent, or Firm* — Panitch Schwarze Belisario & Nadel LLP

(57) ABSTRACT

A conventional syringe defines a longitudinal axis and includes a syringe barrel having a syringe barrel flange laterally extending from an open proximal end of the syringe barrel and a plunger advanceable into the syringe barrel. A rotatable finger flange for such a syringe includes identical first and second flange components, each having an attachment member configured to releasably engage the syringe barrel flange and/or the other flange component, and a flange member laterally extending therefrom. The first and second flange component are engageable and rotatable relative to one another about the longitudinal axis between a non-use position, wherein the first flange member overlies the second flange member to reduce the finger flange footprint, and a use position, wherein the first flange member and the second flange member are angularly spaced apart from one another to provide a finger flange having a greater lateral extent than the syringe barrel flange.

20 Claims, 9 Drawing Sheets

ROTATABLE FINGER FLANGE FOR A SYRINGE

BACKGROUND OF THE INVENTION

The present invention is generally directed to an accessory for a syringe, and, more particularly, to a finger flange removably mountable onto a syringe, and rotatable between a use position and a non-use position.

A syringe is a simple pump utilized for delivering or receiving a substance, e.g., medicament, to/from a recipient or a receptacle. Conventional syringes include a syringe barrel (for holding the substance) having a syringe barrel flange laterally extending from an open proximal end of the syringe barrel and a syringe plunger for advancement into the syringe barrel, or withdrawal through the syringe barrel, through the open proximal end. The syringe flange is often referred to as a "finger flange," because the flange provides a surface which a user can grip or engage with his/her fingers to hold the syringe barrel in place while advancing/retracting the syringe plunger through the barrel.

The size, shape and overall ergonomics of the syringe barrel finger flange can have a direct effect on usability, leverage and control over the syringe. The syringe barrel finger flange on a standard International Organization for Standardization ("ISO") one mL syringe can be inadequate in size, shape and ergonomics. Accordingly, typical finger flange accessories manufactured for removable or permanent mounting onto conventional syringes are larger in size for improved usability, leverage and control over the syringe. However, one drawback associated with such finger flange accessories is that the greater size of the finger flange accessory results in an increased packaging footprint when packaged with the syringe. As a result, there is a direct effect on cost, shipping, storage, etc., which ultimately translates into increased costs for end consumers.

Therefore, it would be advantageous to manufacture a finger flange accessory for a syringe that has a geometry allowing the finger flange to be oriented in a more compact configuration during shipping/transport, i.e., non-use position, having a relatively decreased footprint, and reconfigurable into a use configuration, e.g., at the point of use, having a greater footprint for assisting in improved usability of the syringe. Such a device would provide a user with an improved syringe usage experience, while also minimizing the expense of increased packing size.

BRIEF SUMMARY OF THE INVENTION

Briefly stated, one aspect of the present invention is directed to a rotatable finger flange for a syringe. The syringe defines a longitudinal axis and includes a syringe barrel having a syringe barrel flange laterally extending proximate to an open proximal end of the syringe barrel and a syringe plunger for advancement into the syringe barrel through the open proximal end. The finger flange comprises a first flange component having a first attachment member and a first flange member. The first attachment member is configured to releasably engage the syringe barrel flange and has a first aperture extending therethrough for receiving the syringe therethrough. The first flange member laterally extends from the first attachment member. The rotatable finger flange further comprises a second flange component having a second attachment member and a second flange member. The second attachment member is configured to releasably engage the first attachment member and has a second aperture extending therethrough for receiving the syringe therethrough. The second flange member laterally extends from the second attachment member. The first flange component and the second flange component are engageable and rotatable relative to one another about the longitudinal axis between a non-use position, wherein the first flange member overlies the second flange member to reduce the finger flange footprint, and a use position, wherein the first flange member and the second flange member are angularly spaced apart from one another to provide a finger flange having a greater lateral extent than the syringe barrel flange.

Another aspect of the invention is directed to a rotatable finger flange for use with a syringe. The syringe defines a longitudinal axis and includes a syringe barrel having a syringe barrel flange laterally extending proximate to an open proximal end of the syringe barrel and a syringe plunger for advancement into the syringe barrel through the open proximal end. The finger flange comprises a first flange component having a first attachment member and a first flange member laterally extending from the first attachment member. The first attachment member includes a first base defining a first aperture, a first syringe retention ring extending upwardly from the first base and defining an open upper end having a plurality of angularly spaced radially inwardly extending tabs, a first annular projection extending downwardly from the first aperture and having a first diameter dimensioned to slidably engage the syringe barrel, and a pair of diametrically opposed arcuate projections extending downwardly from the first base, concentric with and spaced from the first annular projection, thereby defining a pair of diametrically opposed arcuate channels therebetween. The first syringe retention ring is dimensioned to releasably receive the syringe barrel flange therein and the radially inwardly extending tabs are configured to flex radially outwardly and snap over the syringe barrel flange upon receiving the syringe barrel flange into the first syringe retention ring, to, in turn, releasably secure the syringe barrel flange. The first aperture is sized and shaped to receive the syringe therethrough.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there are shown in the drawings embodiments which are presently preferred. It should be understood, however, that the disclosure is not limited to the precise arrangements and instrumentalities shown. In the drawings.

DESCRIPTION OF THE DISCLOSURE

Figure 1:
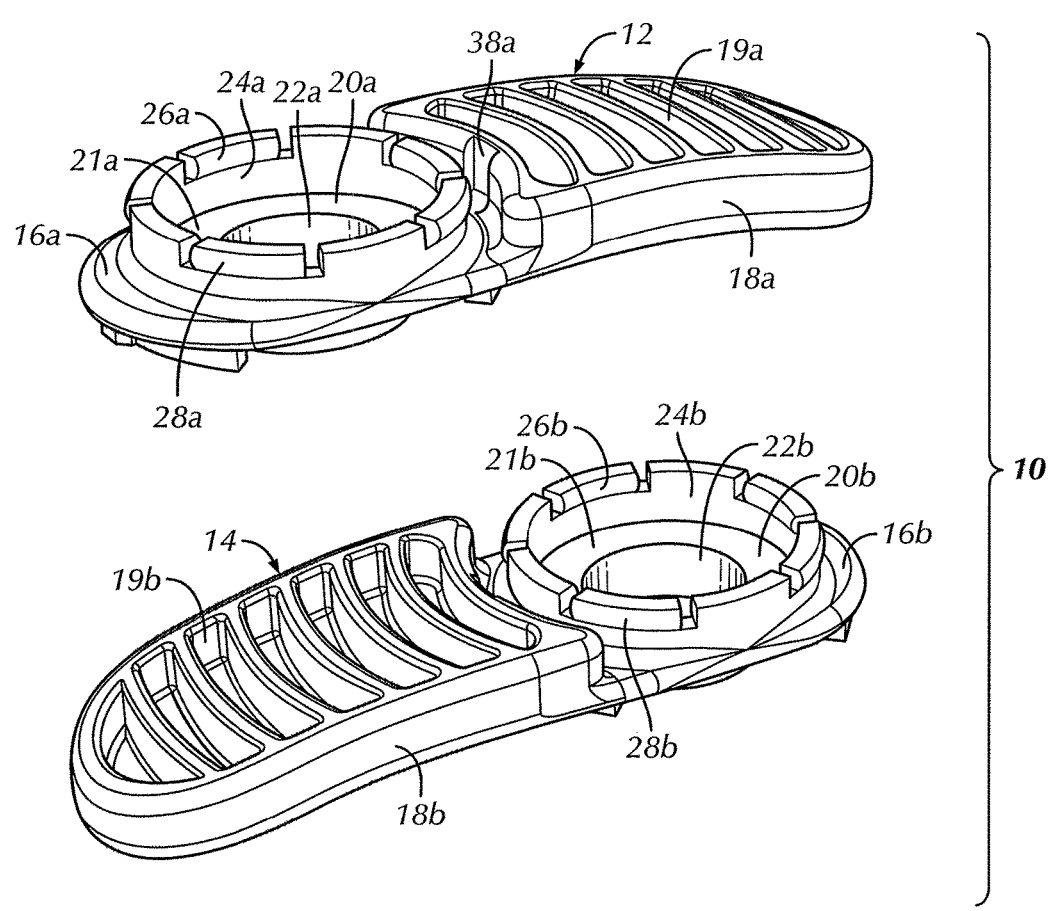
FIG. 1 is a top and side perspective exploded view of a rotatable finger flange, according to a first embodiment of the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the finger flange, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-5B a rotatable finger flange, generally designated 10, according to a first embodiment of the present invention. The finger flange 10 is an accessory or an adapter removably mountable onto a conventional syringe 50, i.e., a separate component from the syringe 50 that can be easily installed onto a portion of the syringe 50 and selectively removed therefrom. However, as should be understood by those of ordinary skill in the art, the rotatable finger flange 10 may alternatively be permanently mounted onto the syringe 50 and/or be an integral component of the syringe 50. As should also be understood by those of ordinary skill in the art, and as shown best in FIGS. 5A and 5B, a conventional syringe 50 comprises a substantially cylindrical syringe barrel 52 having a syringe barrel flange 54 laterally extending proximate to an open proximal end of the syringe barrel 52 and a syringe plunger 56 for advancement into the syringe barrel 52 through the open proximal end. The syringe 50 defines a longitudinal axis Y.

As shown best in FIGS. 1-3B, the rotatable finger flange 10 comprises two identical flange components: a first flange component 12 and a second flange component 14. As will be described further below, the first flange component 12 and the second flange component 14 are mountable onto the syringe 50. When mounted, the first flange component 12 and the second flange component 14 engage one another and are rotatable relative to one another about the longitudinal axis Y of the syringe 50, between a storage or non-use position (FIG. 5A), wherein the first flange component 12 substantially overlies the second flange component 14, a use position (FIG. 5B), wherein the first finger flange component 12 and the second finger flange component 14 are angularly spaced apart from one another while supported by the syringe 50. In the non-use position, the finger flange 10 defines a relatively reduced footprint. In the use position, the finger flange 10 defines a greater lateral extent than the syringe barrel flange 54 to facilitate use of the syringe. As should be understood by those of ordinary skill in the art, and as will be described further below, the rotatable finger flange 10 may be utilized with a single flange component 12.

For the sake of brevity, and since all of the features of the flange components 12, 14 are the same, these features will be described once. When explaining the interaction between the first and second flange components 12, 14, however, the features of the first flange component 12 will be referred to with the suffix "a" and the features of the second flange component 14 will be referred to with the suffix "b."

As shown in FIGS. 1-3B, the flange component 12,14 comprises an attachment member 16 configured to releasably engage the syringe barrel flange 54 and a flange member 18 laterally extending from the attachment member 16. As shown, the flange member 18 includes a plurality of generally arcuate openings 19, to reduce the weight of the flange components 12, 14 and material, thereby reducing cost for consumers. However, as should be understood, the flange member 18 may alternatively comprise a solid flange having no openings. The attachment member 16 includes a base 20, having and upper surface 21 and a lower surface 23, defining a generally centrally disposed aperture 22 extending therethrough, and a syringe retention ring 24 extending outwardly or upwardly from the upper base surface 21. As shown, the syringe retention ring 24 has an open upper end. The aperture 22 is dimensioned to receive a syringe barrel 52 therethrough and the syringe retention ring 24 is dimensioned to releasably receive and secure the syringe barrel flange 54 therein, and to allow the syringe barrel flange 54 to rotate within the retention ring 24 about the longitudinal axis Y.

As shown best in FIG. 1, the syringe retention ring 24 further comprises a plurality of circumferentially angularly spaced apart radially inwardly extending tabs 26 and a plurality of circumferentially angularly spaced apart radially outwardly extending tabs 28 at the open upper end thereof. In the illustrated embodiment, the inwardly extending tabs 26 and the outwardly extending tabs 28 alternate around the circumference of the open upper end of the syringe retention ring 24. However, as should be understood by those of ordinary skill in the art, the inwardly and outwardly extending tabs 26, 28, may be arranged in numerous different orders or patterns, or, alternatively, may be arranged randomly. As will be explained further below, the radially inwardly extending tabs 26 are configured to flex radially outwardly, to snap over a syringe barrel flange 54 upon receiving the barrel flange 54 into the retention ring 24, and, in turn, releasably secure the barrel flange 54 within the retention ring 24. Conversely, the radially outwardly extending tabs 28 are configured to flex radially inwardly, when engaging the first and second flange components 12, 14 together, as also will be explained further below. As shown, both the radially inwardly and outwardly extending taps 26, 28 have radially inward and outward generally arcuate surfaces, respectively, so that the tabs 26, 28 are better suited for sliding into snap connections, as will be described further below.

Figure 2A:
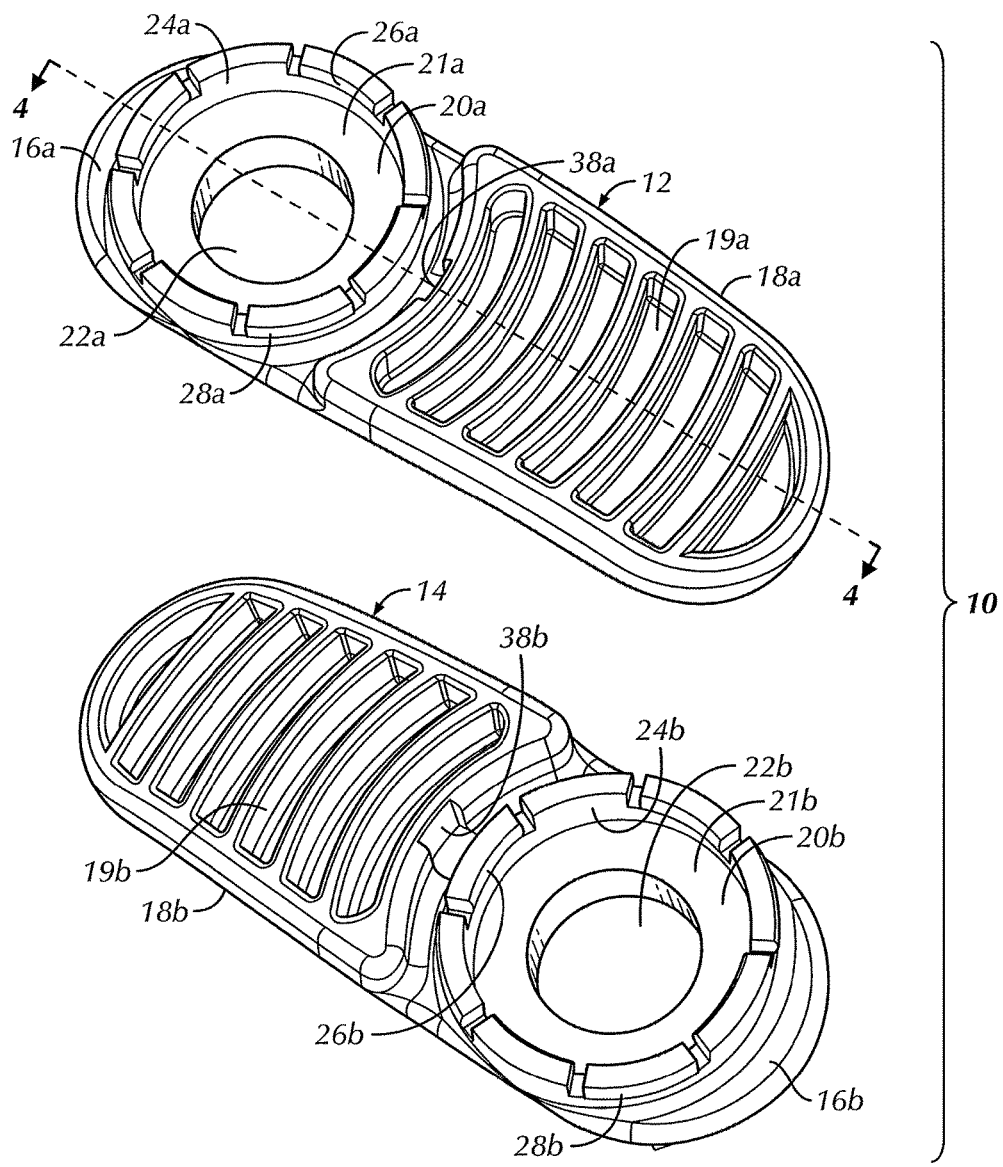
FIG. 2A is a top perspective exploded view of the rotatable finger flange of FIG. 1.
Figure 2B:
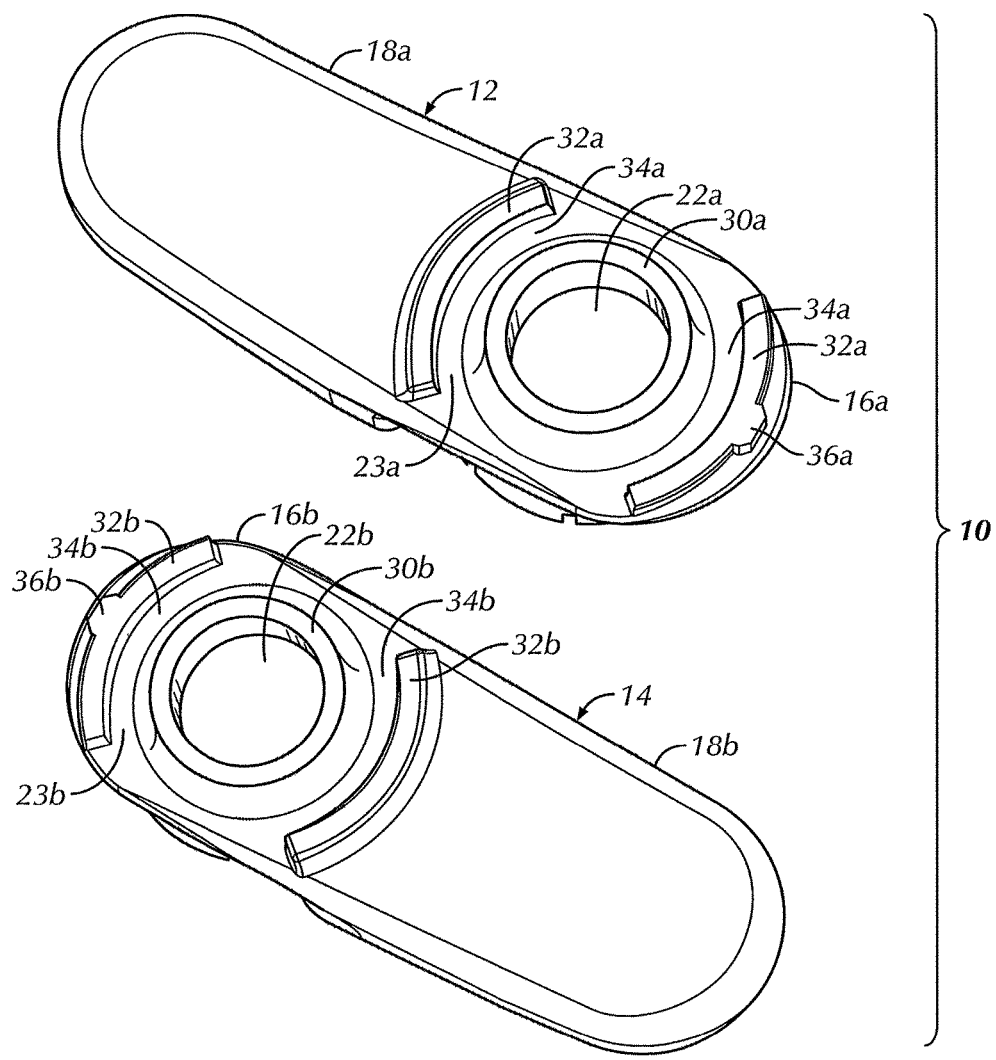
FIG. 2B is a bottom perspective exploded view of the rotatable finger flange of FIG. 1.
Figure 3A:
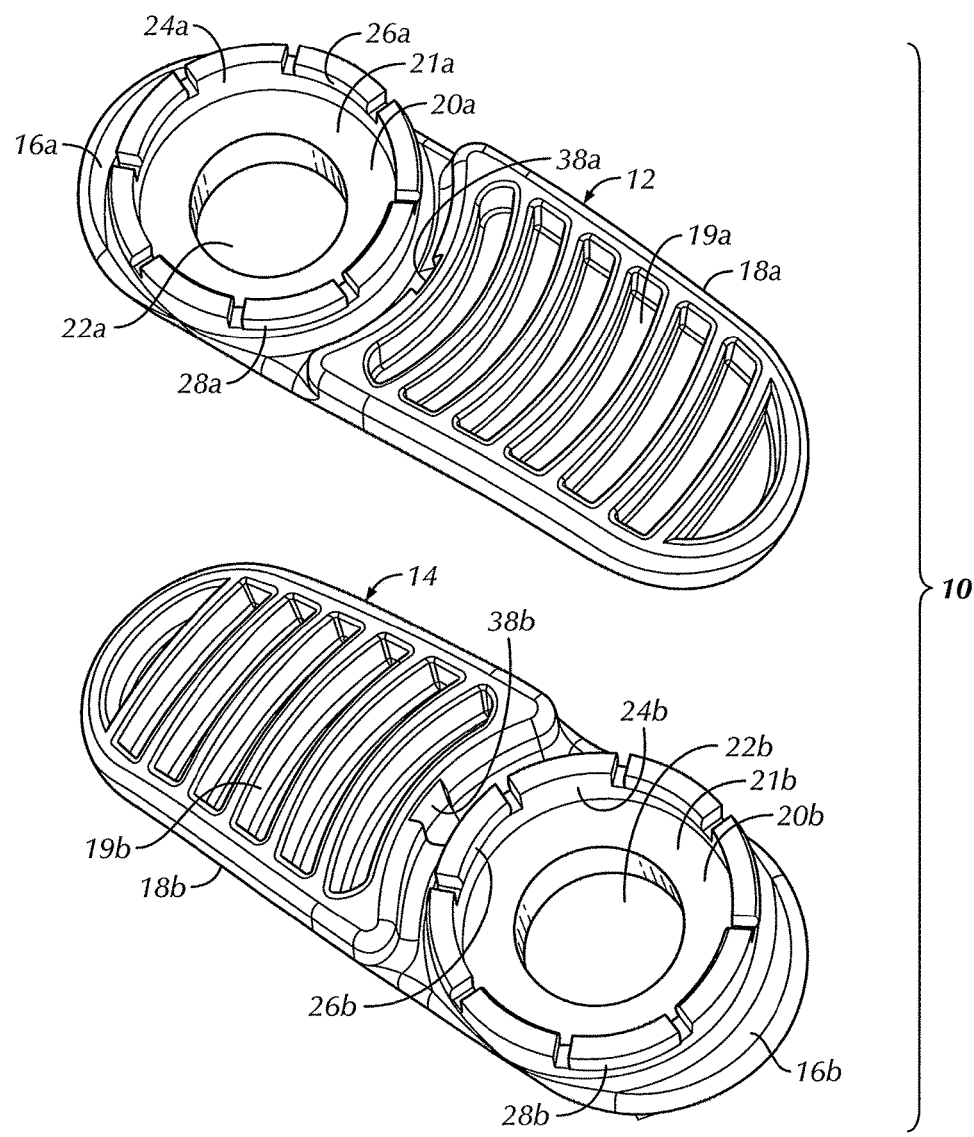
FIG. 3A is a top perspective exploded view of the rotatable finger flange of FIG. 1, having a slightly alternative structure.
Figure 3B:
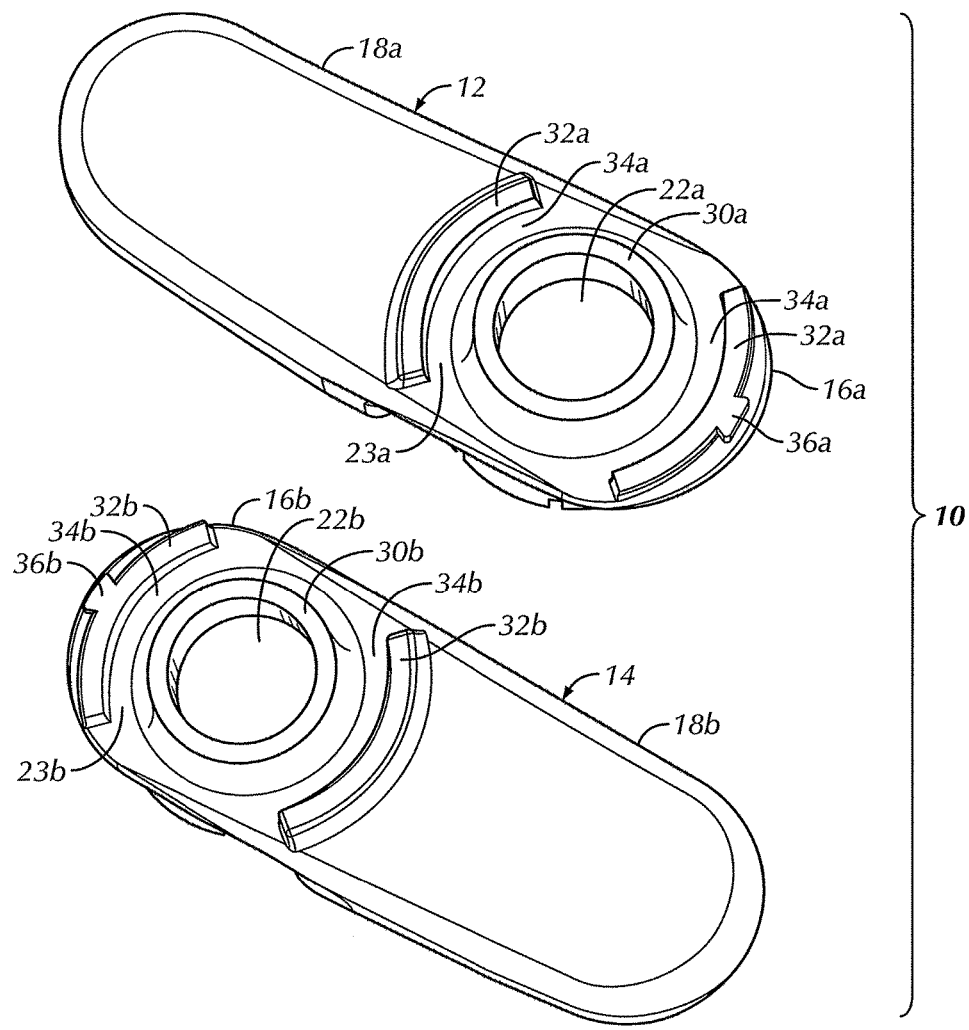
FIG. 3B is a bottom perspective exploded view of the rotatable finger flange of FIG. 3A.
Figures 4, 5A:
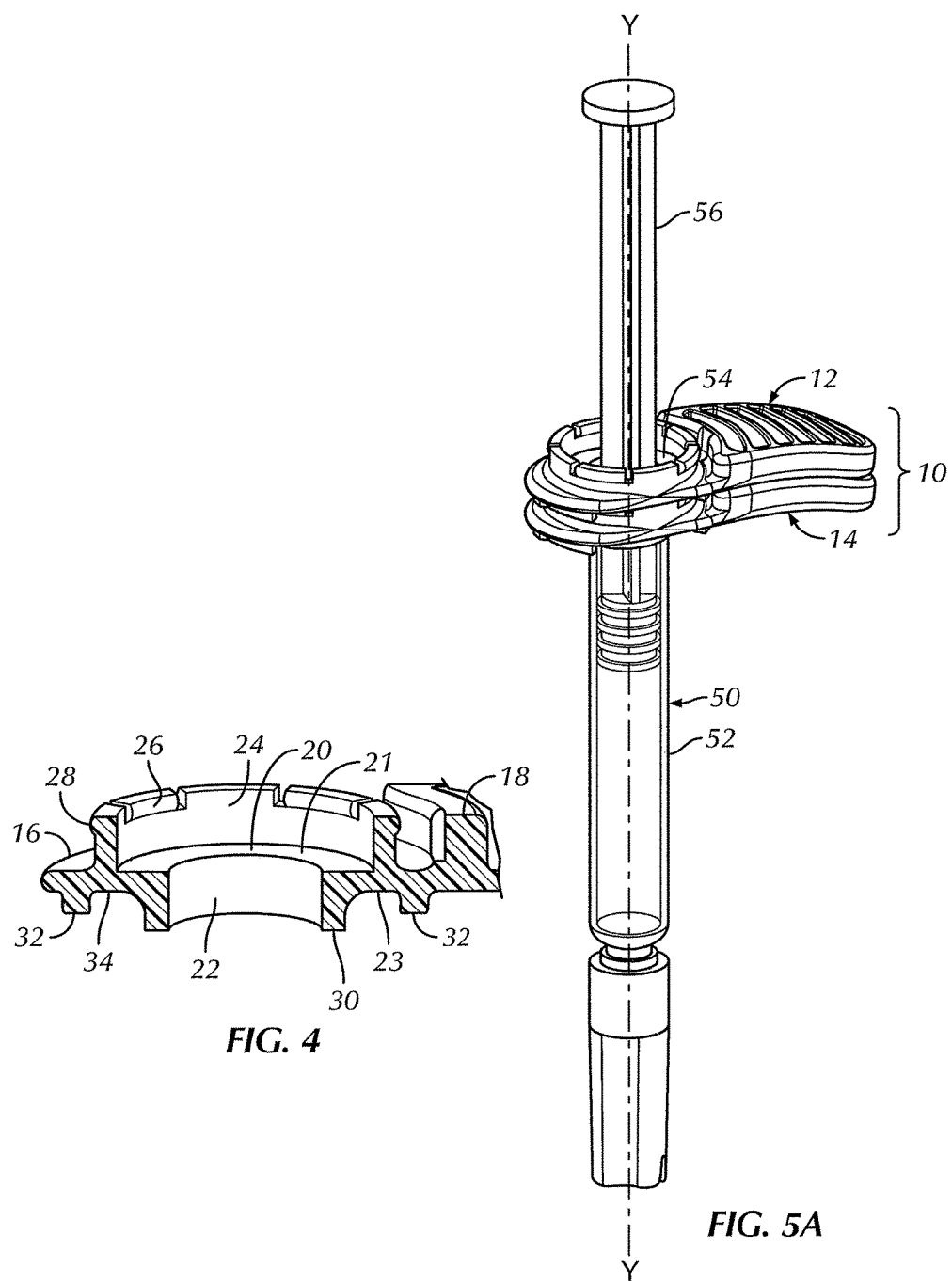
FIG. 4 is a cross-sectional side elevational view of an attachment member of a flange component of the rotatable finger flange of FIG. 1, taken along the sectional line 4-4 of FIG. 2A.
FIG. 5A is a front and side perspective view of a syringe having the rotatable finger flange of FIG. 1 mounted thereon in the non-use position.
Figure 5B:
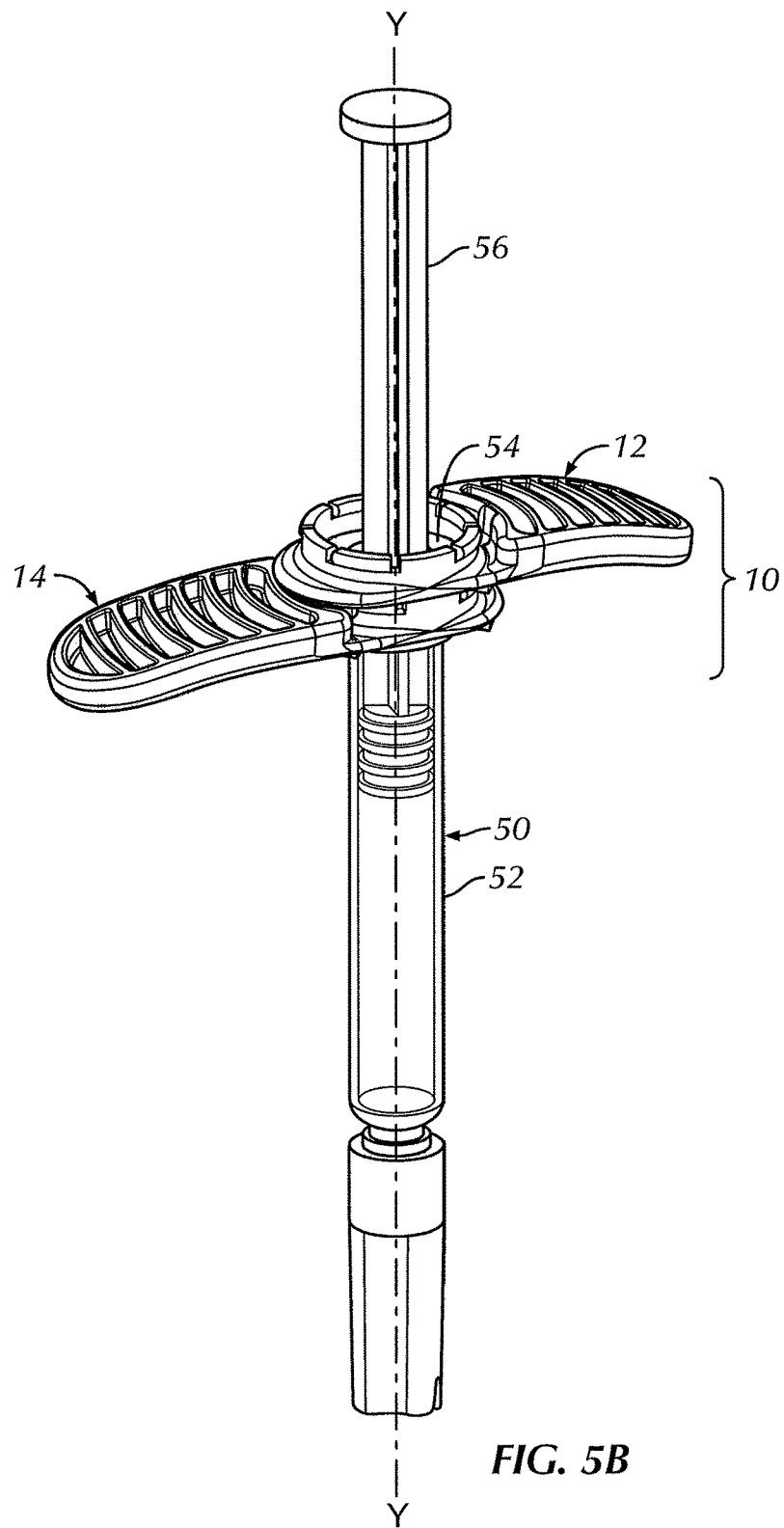
FIG. 5B is a front and side perspective view of a syringe having the rotatable finger flange of FIG. 1 mounted thereon in the use position.

As shown best in FIGS. 2B, 3B, and 4, the attachment member 16 further includes an annular projection 30 extending downwardly from the aperture 22. Accordingly, the annular projection 30 similarly defines a diameter dimensioned to slidably engage the syringe barrel 52. The attachment member 16 further includes a pair of diametrically opposed arcuate projections 32 extending downwardly from the lower base surface 23. The arcuate projections 32 are concentric with, and spaced from, the annular projection 30, thereby defining a pair of diametrically opposed arcuate channels 34 therebetween. The channels 34 are dimensioned to receive the syringe retention ring 24, as will be described further below. As shown best in FIG. 4, the arcuate projections 32 define respective inner surfaces, i.e., the surfaces facing toward the annular projection 30, having a generally concave contour.

To mount the finger flange 10 onto a syringe 50, the syringe barrel 52 is advanced through the aperture 22a of the attachment member 16a of the first flange component 12 with the upper surface 21a facing upward, toward the proximal end of the syringe barrel 52. The syringe barrel 52 is advanced therethrough until the syringe barrel flange 54 contacts the open end of the syringe retention ring 24a of the first flange component 12. The syringe barrel flange 54 is then pressed into the syringe retention ring 24a (or the retention ring 24a is pressed onto the barrel flange 54), such that the radially inwardly extending tabs 26a flex radially outwardly, slide and snap over the syringe barrel flange 54, to releasably secure the syringe barrel flange 54 within the retention ring 24a. Once secured within the retention ring 24a, the first flange component 12 is freely rotatable about the syringe 50, about the longitudinal axis. Y thereof. As should be understood by those of ordinary skill in the art, once the first flange component 12 is mounted onto the syringe 50, the syringe 50 effectively has a single finger flange of a greater extent, providing a user with greater leverage and control over the syringe 50. The user may engage the flange with his/her finger for improved usage of the syringe 50. Thus, the finger flange 10 is usable with a single flange component.

In a preferred embodiment, however, the second flange component 14 is also utilized. Once the first flange component 12 is mounted onto the syringe 50, the syringe barrel 52 is advanced through the aperture 22b of the attachment member 16b of the second flange component 14 with the upper surface 21b of the second flange component 14 facing the lower surface 23a of the first flange component 12. The syringe barrel 52 is advanced therethrough until the annular projection 30a and the arcuate projections 32a of the first flange component 12 (already attached to the syringe barrel flange 54) contact the open end of the syringe retention ring 24b of the second flange component 14. The first and second flange components 12, 14 are then pressed further toward one another, such that the radially outwardly extending tabs 28b of the syringe retention ring 24b of the second flange component 14 flex radially inwardly and snap into complimentary engagement with the generally concave contour of the inner surfaces of the arcuate projections 32a, and the open end of the syringe retention ring 24b is received within the arcuate channels 34a of the first flange component 12. Thus, both the first and second flange components 12, 14 are mounted onto the syringe 50 and a rotational connection is established between the first flange component 12 and the second flange component 14. As should be understood by those of ordinary skill in the art, however, the first and second flange components 12, 14 may alternatively be engaged with one another first, and then mounted onto the syringe 50 afterwards.

As shown, once the first flange component 12 and the second flange component 14 are rotatably engaged, they can be rotated with respect to one another between the non-use position (FIG. 5A) in which the entire first flange member 18a is aligned with, and overlies, the second flange member 18b, and the use position (FIG. 5B), in which the flange members 18a, 18b, are angularly displaced. When rotated with respect to one another, the syringe retention ring 24b of the second flange component 14 rotationally slides within the arcuate channels 34a of the first flange component 12. As shown, the first and second flange components 12, 14 substantially overlap one another in the non-use position. Thus, the syringe 50 and the finger flange 10, including both the first and second flange components 12, 14, can be packaged with the finger flange 10 in the non-use position, in order to minimize the packaging footprint. Thereafter, when the syringe 50 and the finger flange 10 are removed from the packaging for use, the first and second flange components 12, 14 may be rotated about the longitudinal axis Y, to be angularly spaced from one another, into the use position. In the use position, the syringe 50 effectively has a finger flange of a greater extent, providing a user with greater leverage and control over the syringe 50. The user may engage the flange with his/her fingers for improved usage of the syringe 50.

In the illustrated embodiment, the first and second flange components 12, 14 are angularly spaced approximately 180 degrees from one another in the use position. However, as should be understood by those of ordinary skill in the art, the first and second flange components 12, 14, may alternatively be angularly spaced apart in numerous different angular degrees in the use position, according to different applications and space requirements. For example, without limitation, the first and second flange members 12, 14 may be angularly spaced apart approximately 90 degrees in the use position.

As shown in FIGS. 2A-3B, the first and second flange components 12, 14, lock into the use position, such that the flange components 12, 14, do not rotate during use of the syringe 50. Additionally, once the flange components 12, 14, lock, a user will be ensured that the components 12, 14 are in the proper use position. At least one of the arcuate projections 32 of the attachment member 16 includes a radially outwardly extending tab 36 and the flange member 18 includes a complimentary slot 38 at an inner end thereof (adjacent the attachment member 16). The radially outwardly extending tab 36 mates with the slot 38 for locking together the flange components 12, 14 in the use position.

In some embodiments, as shown in FIGS. 3A and 3B, the first and second flange components 12, 14 permanently lock into the use position. That is, once the flange components 12, 14 are locked into the use position, i.e., the tab 36 mates with the slot 38, they are not intended to be disengaged, and forceful rotation out of the use position may break component(s) of either of the flange components 12, 14. As shown in FIG. 3B, the tab 36 defines a generally isosceles trapezoidal geometry, wherein the distal base is wider than the opposing inner base thereof, attached to the arcuate projection 32. As shown in FIG. 3A the complimentary slot 38 in the flange member 18 defines a similarly sized generally isosceles trapezoidal geometry, wherein the inner base, deeper into the flange member 18, is wider than the opposing outer base. Accordingly, the angled lateral legs of the tab 36 and the slot 38 allow the tab 36 to engage the slot 38, but prevent the tab 36 from thereafter disengaging from the slot 38. Thus, when the syringe 50 and the finger flange 10 are removed from the packaging for use, the first and second flange components 12, 14 may be rotated about the longitudinal axis Y, to be angularly spaced from one another, into the use position, wherein the tab 36a of the first flange component 12 will engage the slot 38b of the second flange component. Thereafter, the first and second flange components cannot be returned back to the non-use position.

In alternative embodiments, as shown in FIGS. 2A-2B, the first and second flange components 12, 14 releasably lock into the use position. That is, the tab 36 engages the slot 38 in the use position to stabilize the first and second flange components 12, 14 relative to one another, but the tab 36 and slot 38 are configured such that they may be disengaged, e.g., to return the first and second flange components 12, 14 to the non-use position. As shown in FIG. 2B, the tab 36 defines a generally isosceles trapezoidal geometry, wherein the distal base is narrower than the opposing inner base thereof, attached to the arcuate projection 32. Further, the lateral legs thereof define substantially rounded ends. As shown in FIG. 2A the slot 38 in the flange member 18 defines a generally rectangular geometry. Accordingly, the tab 36 and the slot 38 are engageable, and the angled lateral legs having rounded ends of the tab 36 allow the tab 36 to also slide out of engagement with the slot 38. Thus, when the syringe 50 and the finger flange 10 are removed from the packaging for use, the first and second flange components 12, 14 may be rotated about the longitudinal axis Y, to be angularly spaced from one another, into the use position, wherein the tab 36a of the first flange component 12 will engage the slot 38b of the second flange component. Thereafter, after using the syringe 50, a user may desire to revert the finger flange 10 back to the non-use position, and the first and second flange components 12, 14 can returned back to the non-use position. As should be understood by those of ordinary skill in the art, the first and second flange components 12, 14, may additionally, or alternatively, include complementary tab and slot components that allow the flange components 12, 14 to be removably locked into the non-use position as well.

To disengage the first and second flange components 12, 14 from one another and from the syringe 50, the reverse steps are generally performed. That is, the first and second flange components 12, 14 are pulled apart from one another, such that the radially outwardly extending tabs 28b of the syringe retention ring 24b of the second flange component 14 flex radially inwardly and snap out of complimentary engagement with the generally concave contour of the inner surfaces of the arcuate projections 32a of the first flange component 12. Similarly, the first flange component 12 is pulled away from the syringe barrel flange 54, such that the radially inwardly extending tabs 26a flex radially outwardly, slide and snap out of engagement with the syringe barrel flange 54. As should be understood by those of ordinary skill in the art, the first and second flange components 12, 14 may be disengaged first, prior to disengaging the first flange component 12 from the syringe flange 54, or the first flange component 12 (with the second flange component 14 attached) may be disengaged from the syringe flange 54 first, and thereafter the flange components 12, 14 are disengaged.

Figure 6A:
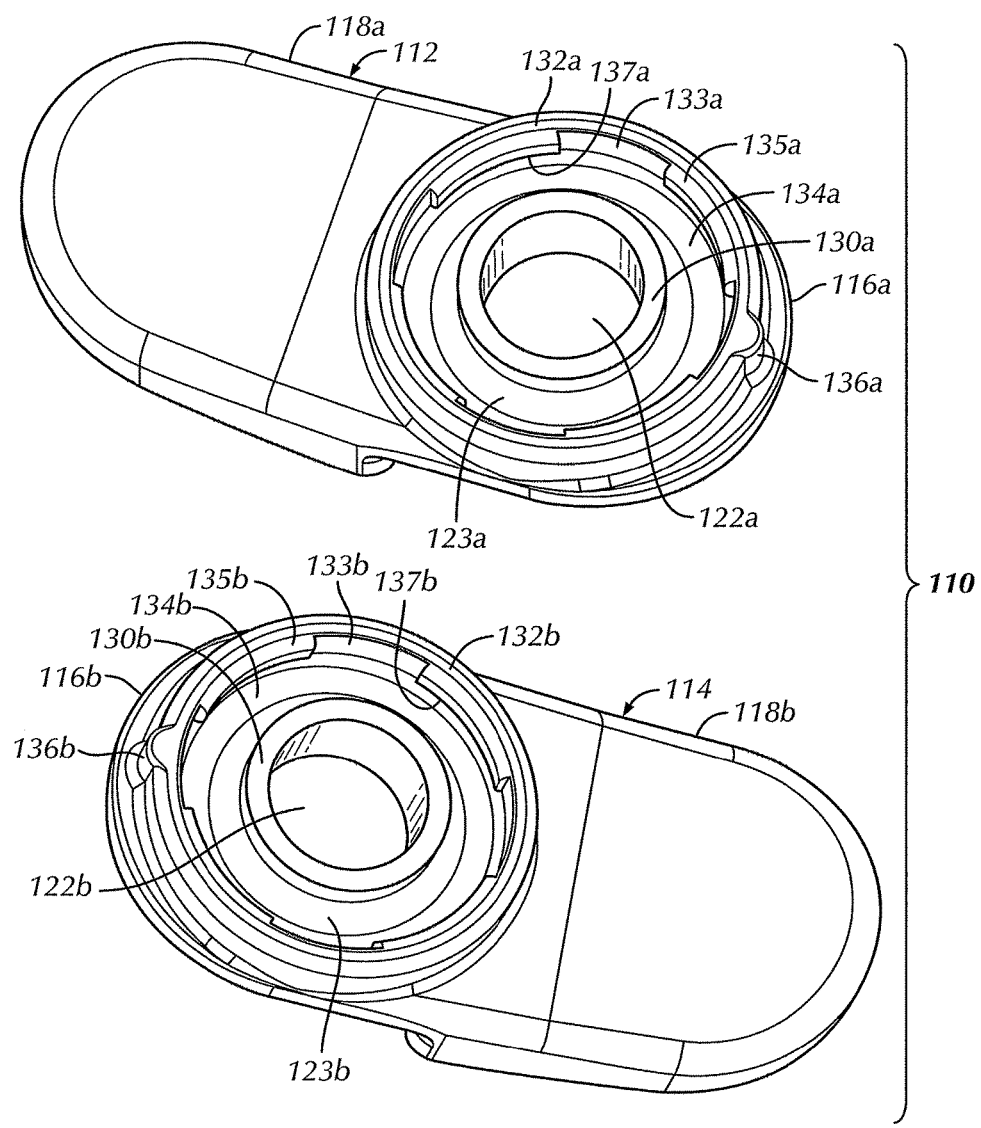
FIG. 6A is a bottom perspective exploded view of a rotatable finger flange, according to a second embodiment of the present disclosure.
Figure 6B:
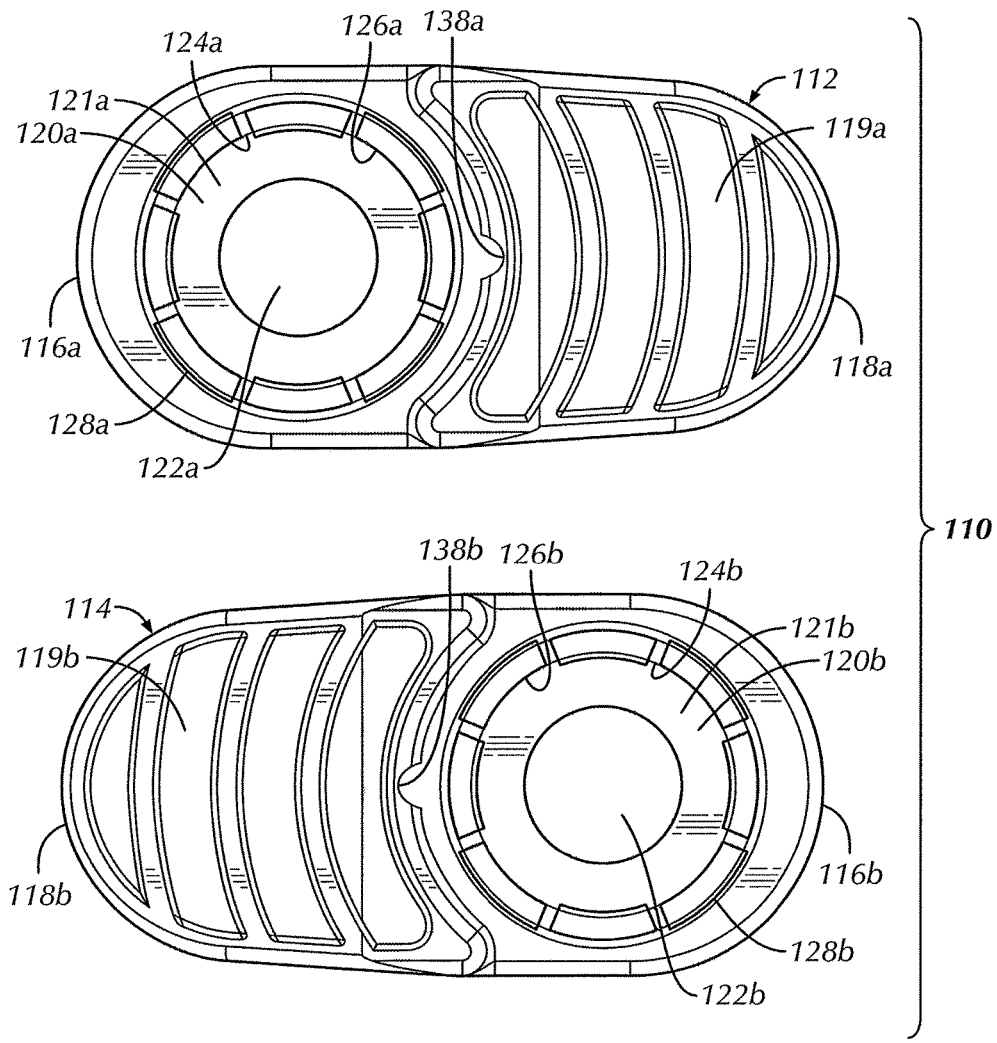
FIG. 6B is a top plan exploded view of the rotatable finger flange of FIG. 6A.

FIGS. 6A-6B show a second embodiment of a rotatable finger flange 110. The reference numerals of the second embodiment are distinguishable from those of the first embodiment by a factor of one-hundred (100), but otherwise indicate the same elements as indicated in the above-described first embodiment, except as otherwise specified.

The rotatable finger flange 110 of the second embodiment is substantially similar to that of the first embodiment. The description of certain similarities between the embodiments may be omitted herein for the sake of brevity and convenience, and, therefore, is not limiting. Also, since all of the features of the flange components 112, 114 are the same, these features will be described once. However, when explaining the interaction between the first and second flange components 112, 114, the features of the first flange component 112 will be referred to with the suffix "a" and the features of the second flange component 114 will be referred to with the suffix "b."

A distinguishing feature of the second embodiment is that the pair of diametrically opposed arcuate projections 32 are replaced with a single outer annular projection 132 extending downwardly from the lower base surface 123 to an open bottom end. The outer annular projection 132 is concentric with, and spaced from, the inner annular projection 130, thereby defining a single annular channel 134 therebetween.

Instead of, or in addition to, having a generally concave inner contour, the outer annular projection 132 includes a plurality of circumferentially angularly spaced apart cutouts 133 along the inner surface thereof. The cutouts 133 extend down substantially the entire projection length of the outer annular projection 132, and are each dimensioned to receive a respective outwardly extending tab 128 of a syringe retention ring 124, when engaging the flange components 112, 114, as described further below. The cutouts 133 alternate around the circumference of the outer annular projection 132 with a plurality of circumferentially angularly spaced apart radially inwardly extending tabs 135. The tabs 135 are located at the open bottom end of the outer annular projection 132, such that a respective slot 137 is defined between the lower base surface 123 and each tab 135, to assist in engagement of flange components 112, 114, as described further below.

The flange component 112 is mountable onto a syringe 50 in the same manner as the flange component 12, and the finger flange 110 is similarly usable with a single flange component as with the finger flange 10. In the preferred embodiment, however, the second flange component 114 is also utilized. Once the first flange component 112 is mounted onto the syringe 50, as described above, the syringe barrel 52 is advanced through the aperture 122b of the attachment member 116b of the second flange component 114 with the upper surface 121b of the second flange component 114 facing the lower surface 123a of the first flange component 112. The syringe barrel 52 is advanced therethrough until the inner annular projection 130a and the outer annular projection 132a of the first flange component 112 (already attached to the syringe barrel flange 54) contacts the open top end of the syringe retention ring 124b of the second flange component 114.

The first and second flange components 112, 114 are then rotated with respect to one another about the syringe barrel 52 until the radially outwardly extending tabs 128b of the syringe retention ring 124b of the second flange component 114 align with the cutouts 133a in the outer annular projection 132a of the first flange component 112. The second flange component 114 is then further advanced toward the first flange component 112, such that the tabs 128b advance through the cutouts 133a until the radially outwardly extending tabs 128b contact the lower base surface 123a of the first flange component 112 and the open end of the syringe retention ring 124b is received within the annular channel 134a of the first flange component 112. The first and second flange components 112, 114 are then rotated again with respect to one another about the syringe barrel 52, such that the radially outwardly extending tabs 128b of the second flange component 114 are received within the slots 137a of the first flange component 112. The tabs 135a of the first flange component 112, bordering the slots 137a, act as a catch for the tabs 128b, thereby retaining together the first and second flange components 112, 114.

Thus, both the first and second flange components 112, 114 are mounted onto the syringe 50 and a rotational connection is established between the first flange component 112 and the second flange component 114. Once the first flange component 112 and the second flange component 114 are rotatably engaged, the two flange components 112, 114 are rotated with respect to one another between the non-use position and the use position, as described above in the first embodiment.

The finger flange 110 may alternatively include the tabs 135 and slots 137, without the cutouts 133 (not shown). Accordingly, when assembling the first and second flange components 112, 114 together, the outer annular projection 132a biases the radially outwardly extending tabs 128b of the second flange component 114 to flex radially inwardly when engaging the outer annular projection 132a. The first and second flange components 112, 114 are then rotated again with respect to one another about the syringe barrel 52, such that tabs 128b of the second flange component 114, which are radially inwardly flexed, are received within the slots 137a of the first flange component 112.

Similarly to FIGS. 2A and 2B, the first and second flange components 112, 114 releasably lock into the use position. That is, the tab 136 engages the slot 138 in the use position to stabilize the first and second flange components 112, 114 relative to one another, but the tab 136 and slot 138 are configured such that they may be disengaged, e.g., to return the first and second flange components 112, 114 to the non-use position. As shown in FIG. 6A, the tab 136 defines a generally arcuate geometry. As shown in FIG. 6B the slot 138 in the flange member 118 defines a complimentary arcuate geometry. Accordingly, the complimentary arcuate surfaces of the tab 136 and the slot 138 allow for generally smooth engagement and disengagement. As should be understood, however, the finger flange 110 may include a tab 136 and a slot 138 having differing geometry, such as, without limitation, as described in the first embodiment, for example.

To disengage the first and second flange components 112, 114 from one another and from the syringe 50, the reverse steps are generally performed. That is, the first and second flange components 112, 114 are rotated with respect to one another about the syringe barrel 52, such that the radially outwardly extending tabs 128b of the syringe retention ring 124b of the second flange component 114 realign with the cutouts 133a in the outer annular projection 132a of the first flange component 112. The second flange component 114 may then be withdrawn from the first flange component 112. The first flange component 112 is then pulled away from the syringe barrel flange 54, in the same manner as described above with respect to the first flange component 12. As should be understood by those of ordinary skill in the art, the first and second flange components 112, 114 may initially be disengaged, prior to disengaging the first flange component 112 from the syringe flange 54, or the first flange component 112 (with the second flange component 114 attached) may be initially disengaged from the syringe flange 54, and thereafter the flange components 112, 114 are disengaged from each other.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

We claim:

1. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising:
   a first flange component having a first attachment member configured to releasably engage the syringe barrel flange and having a first aperture extending therethrough for receiving the syringe therethrough, and a first flange member laterally extending from said first attachment member; and
   a second flange component having a second attachment member configured to releasably engage the first attachment member and having a second aperture extending therethrough for receiving the syringe therethrough, and a second flange member laterally extending from said second attachment member;
   wherein the first flange component and the second flange component are engageable and rotatable relative to one another about the longitudinal axis between a non-use position, wherein (i) the first aperture overlies the second aperture along the longitudinal axis and (ii) the first flange member overlies the second flange member along the longitudinal axis, and a use position, wherein (i) the first aperture overlies the second aperture along the longitudinal axis and (ii) the first flange member and the second flange member are angularly spaced apart from one another to provide a finger flange having a greater lateral extent than the syringe barrel flange.

2. The rotatable finger flange of claim 1, wherein the first flange member is angularly spaced approximately 180 degrees from the second flange member in the use position.

3. The rotatable finger flange of claim 1, wherein the first attachment member of the first flange component comprises a first base defining the first aperture and having a first syringe retention ring extending upwardly from said first base and defining an open upper end, wherein said first syringe retention ring is dimensioned to releasably secure the syringe barrel flange therein.

4. The rotatable finger flange of claim 3, wherein the first syringe retention ring comprises a plurality of angularly spaced radially inwardly extending tabs at the open upper end thereof, wherein said radially inwardly extending tabs are configured to flex radially outwardly and snap over the syringe barrel flange upon receiving the syringe barrel flange into the first syringe retention ring, to, in turn, releasably secure the syringe barrel flange within the first syringe retention ring.

5. The rotatable finger flange of claim 3, wherein the first attachment member of the first flange component further comprises a first annular projection extending downwardly from the first aperture and having a first diameter dimensioned to slidably engage the syringe barrel.

6. The rotatable finger flange of claim 5, wherein the first attachment member of the first flange component further comprises a pair of diametrically opposed arcuate projections extending downwardly from the first base, concentric with, and spaced from, the first annular projection, thereby defining a pair of diametrically opposed arcuate channels therebetween.

7. The rotatable finger flange of claim 6, wherein the arcuate projections define respective inner surfaces facing toward the first annular projection, said inner surfaces having a generally concave contour.

8. The rotatable finger flange of claim 6, wherein the second attachment member of the second flange component comprises a second base defining the second aperture and having a second syringe retention ring extending upwardly from said second base and defining an open upper end.

9. The rotatable finger flange of claim 8, wherein the second syringe retention ring comprises a plurality of angularly spaced radially outwardly extending tabs at the open upper end thereof, wherein said radially outwardly extending tabs of the second attachment member are configured to mate with the arcuate channels of the first attachment member.

10. The rotatable finger flange of claim 5, wherein the first annular projection is a first, inner annular projection, and the first attachment member of the first flange component further comprises a first, outer annular projection extending downwardly from the first base, concentric with, and spaced from, the first, inner annular projection, thereby defining an annular channel therebetween.

11. The rotatable finger flange of claim 10, wherein the first, outer annular projection comprises a plurality of angularly spaced cutouts along an inner surface thereof and a plurality of angularly spaced tabs, extending radially inwardly from the inner surface, wherein the cutouts and the radially inwardly extending tabs of the first, outer annular projection alternate around a circumference of the first, outer annular projection, and wherein a slot is defined between the first base and each respective radially inwardly extending tab of the first, outer annular projection.

12. The rotatable finger flange of claim 11, wherein the second attachment member of the second flange component comprises a second base defining the second aperture and having a second syringe retention ring extending upwardly from said second base and defining an open upper end and the second syringe retention ring comprises a plurality of angularly spaced radially outwardly extending tabs at the open upper end thereof, wherein said radially outwardly extending tabs of the second attachment member are configured to mate with the annular channel of the first attachment member.

13. The rotatable finger flange of claim 12, wherein the radially outwardly extending tabs of the second syringe retention ring of the second flange member are configured to advance through the cutouts of the first, outer annular projection, and the first flange component and the second flange component are thereafter rotatable with respect to one another about the longitudinal axis, such that the radially outwardly extending tabs of the second syringe retention ring of the second flange member enter into the slots between the first base and each respective radially inwardly extending tab of the first, outer annular projection, to, in turn, establish a rotating connection.

14. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising:
a first flange component having a first attachment member configured to releasably engage the syringe barrel flange and having a first aperture extending therethrough for receiving the syringe therethrough, and a first flange member laterally extending from said first attachment member; and
a second flange component having a second attachment member configured to releasably engage the first attachment member and having a second aperture extending therethrough for receiving the syringe therethrough, and a second flange member laterally extending from said second attachment member;
wherein the first flange component and the second flange component are engageable and rotatable relative to one another about the longitudinal axis between a non-use position, wherein the first flange member overlies the second flange member, and a use position, wherein the first flange member and the second flange member are angularly spaced apart from one another to provide a finger flange having a greater lateral extent than the syringe barrel flange,
wherein the first attachment member of the first flange component comprises a first base defining the first aperture and having a first syringe retention ring extending upwardly from said first base and defining an open upper end, wherein said first syringe retention ring is dimensioned to releasably secure the syringe barrel flange therein,
wherein the first syringe retention ring comprises a plurality of angularly spaced radially inwardly extending tabs at the open upper end thereof, wherein said radially inwardly extending tabs are configured to flex radially outwardly and snap over the syringe barrel flange upon receiving the syringe barrel flange into the first syringe retention ring, to, in turn, releasably secure the syringe barrel flange within the first syringe retention ring, and
wherein the first syringe retention ring further comprises a plurality of angularly spaced radially outwardly extending tabs at the open upper end, and the radially inwardly extending tabs and the radially outwardly extending tabs alternate around the open upper end of the first syringe retention ring.

15. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising:
a first flange component having a first attachment member configured to releasably engage the syringe barrel flange and having a first aperture extending therethrough for receiving the syringe therethrough, and a first flange member laterally extending from said first attachment member; and
a second flange component having a second attachment member configured to releasably engage the first attachment member and having a second aperture extending therethrough for receiving the syringe therethrough, and a second flange member laterally extending from said second attachment member;
wherein the first flange component and the second flange component are engageable and rotatable relative to one another about the longitudinal axis between a non-use position, wherein the first flange member overlies the second flange member, and a use position, wherein the first flange member and the second flange member are angularly spaced apart from one another to provide a finger flange having a greater lateral extent than the syringe barrel flange, wherein the first attachment member of the first flange component further comprises a first annular projection extending downwardly from the first aperture and having a first diameter dimensioned to slidably engage the syringe barrel, wherein the first attachment member of the first flange component further comprises a pair of diametrically opposed arcuate projections extending downwardly from the first base, concentric with, and spaced from, the first annular projection, thereby defining a pair of diametrically opposed arcuate channels therebetween, wherein the second attachment member of the second flange component comprises a second base defining the second aperture and having a second syringe retention ring extending upwardly from said second base and defining an open upper end, wherein the second syringe retention ring comprises a plurality of angularly spaced radially outwardly extending tabs at the open upper end thereof, wherein said radially outwardly extending tabs of the second attachment member are configured to mate with the arcuate channels of the first attachment member, and wherein the arcuate projections define respective inner surfaces facing toward the first annular projection, said inner surfaces having a concave contour, and wherein the radially outwardly extending tabs of the second syringe retention ring of the second flange member are configured to flex radially inwardly and snap into the arcuate channels of the first flange member to, in turn, establish a rotating connection.

16. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising:

a first flange component having a first attachment member configured to releasably engage the syringe barrel flange and having a first aperture extending therethrough for receiving the syringe therethrough, and a first flange member laterally extending from said first attachment member; and a second flange component having a second attachment member configured to releasably engage the first attachment member and having a second aperture extending therethrough for receiving the syringe therethrough, and a second flange member laterally extending from said second attachment member;

wherein the first flange component and the second flange component are engageable and rotatable relative to one another about the longitudinal axis between a non-use position, wherein the first flange member overlies the second flange member, and a use position, wherein the first flange member and the second flange member are angularly spaced apart from one another to provide a finger flange having a greater lateral extent than the syringe barrel flange, wherein the first attachment member of the first flange component further comprises a first annular projection extending downwardly from the first aperture and having a first diameter dimensioned to slidably engage the syringe barrel, wherein the first attachment member of the first flange component further comprises a pair of diametrically opposed arcuate projections extending downwardly from the first base, concentric with, and spaced from, the first annular projection, thereby defining a pair of diametrically opposed arcuate channels therebetween, and wherein at least one of the arcuate projections of the first attachment member of the first flange component includes a radially outwardly extending tab, and the second flange member of the second flange component includes a complimentary slot at an inner end thereof, wherein the radially outwardly extending tab of the first flange component is configured to releasably mate with the complimentary slot of the second flange component in the use position.

17. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising:

a first flange component having a first attachment member configured to releasably engage the syringe barrel flange and having a first aperture extending therethrough for receiving the syringe therethrough, and a first flange member laterally extending from said first attachment member; and a second flange component having a second attachment member configured to releasably engage the first attachment member and having a second aperture extending therethrough for receiving the syringe therethrough, and a second flange member laterally extending from said second attachment member;

wherein the first flange component and the second flange component are engageable and rotatable relative to one another about the longitudinal axis between a non-use position, wherein the first flange member overlies the second flange member, and a use position, wherein the first flange member and the second flange member are angularly spaced apart from one another to provide a finger flange having a greater lateral extent than the syringe barrel flange, wherein the first attachment member of the first flange component further comprises a first annular projection extending downwardly from the first aperture and having a first diameter dimensioned to slidably engage the syringe barrel, wherein the first attachment member of the first flange component further comprises a pair of diametrically opposed arcuate projections extending downwardly from the first base, concentric with, and spaced from, the first annular projection, thereby defining a pair of diametrically opposed arcuate channels therebetween, and wherein at least one of the arcuate projections of the first attachment member of the first flange component includes a radially outwardly extending tab, and the second flange member of the second flange component includes a complimentary slot at an inner end thereof, wherein the radially outwardly extending tab of the first flange component is configured to permanently mate with the complimentary slot of the second flange component in the use position.

18. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising a first flange component having a first attachment member and a first flange member laterally extending from said first attachment member, said first attachment member including a first base defining:
a first aperture,
a first syringe retention ring extending upwardly from said first base and defining an open upper end having a plurality of angularly spaced radially inwardly extending tabs,
a first annular projection extending downwardly from the first aperture and having a first diameter dimensioned to slidably engage the syringe barrel, and
a pair of diametrically opposed arcuate projections extending downwardly from the first base, concentric with and spaced from the first annular projection, thereby defining a pair of diametrically opposed arcuate channels between the arcuate projections and the first annular projection, respectively;
wherein said first syringe retention ring is dimensioned to releasably receive the syringe barrel flange therein and said radially inwardly extending tabs are configured to flex radially outwardly and snap over the syringe barrel flange upon receiving the syringe barrel flange into the first syringe retention ring, to, in turn, releasably secure the syringe barrel flange, and said first aperture is sized and shaped to receive the syringe therethrough.

19. A rotatable finger flange for use with a syringe defining a longitudinal axis and including a syringe barrel having a syringe barrel flange laterally extending proximate to an open proximal end of the syringe barrel and a syringe plunger for advancement into the syringe barrel through the open proximal end, the finger flange comprising:
a first flange component having a first attachment member and a first flange member laterally extending from said first attachment member, said first attachment member including a first base defining:
a first aperture,
a first syringe retention ring extending upwardly from said first base and defining an open upper end having a plurality of angularly spaced radially inwardly extending tabs,
a first annular projection extending downwardly from the first aperture and having a first diameter dimensioned to slidably engage the syringe barrel, and
a pair of diametrically opposed arcuate projections extending downwardly from the first base, concentric with and spaced from the first annular projection, thereby defining a pair of diametrically opposed arcuate channels therebetween;
wherein said first syringe retention ring is dimensioned to releasably receive the syringe barrel flange therein and said radially inwardly extending tabs are configured to flex radially outwardly and snap over the syringe barrel flange upon receiving the syringe barrel flange into the first syringe retention ring, to, in turn, releasably secure the syringe barrel flange, and said first aperture is sized and shaped to receive the syringe therethrough; and
a second flange component having a second attachment member and a second flange member laterally extending from said second attachment member, said second attachment member including a second base defining:
a second aperture,
a second syringe retention ring extending upwardly from said second base and defining an open upper end having a plurality of angularly spaced radially outwardly extending tabs,
a second annular projection extending downwardly from the second aperture and having a second diameter dimensioned to slidably engage the syringe barrel;
wherein said radially outwardly extending tabs of the second syringe retention ring are configured to flex radially inwardly and snap into the arcuate channels of the first flange member for a pivoting connection between the first flange component and the second flange component, and said second aperture is sized and shaped to receive the syringe therethrough.

20. The rotatable finger flange of claim 19, wherein the first flange component and the second flange component are engageable and rotatable relative to one another about the longitudinal axis between a non-use position, wherein the first flange member overlies the second flange member, and a use position, wherein the first flange member and the second flange member are angularly spaced apart from one another to provide a finger flange having a greater lateral extent than the syringe barrel flange.

* * * * *